United States Patent [19]
Joly et al.

[11] Patent Number: 6,147,269
[45] Date of Patent: *Nov. 14, 2000

[54] ISOMERIZATION WITH AN EUO-TYPE CATALYST OF AROMATIC COMPOUNDS WITH EIGHT CARBON ATOMS FOLLOWED BY A DEHYDROGENATION STAGE

[75] Inventors: Jean-François Joly; Vincent Coupard, both of Lyons; Julia Magne-Drisch, Vilette de Vienne; Fabio Alario, Neully sur Seine; Elisabeth Merlen; Sylvie Lacombe, both of Rueil-malmaison; Eric Benazzi, Chatou, all of France

[73] Assignee: Institut Francais du Petrole, Rueil Malmaison Cedex, France

[ * ] Notice: This patent is subject to a terminal disclaimer.

[21] Appl. No.: 09/289,662

[22] Filed: Apr. 12, 1999

[30] Foreign Application Priority Data

Apr. 10, 1998 [FR] France ................................. 98 04650

[51] Int. Cl.[7] .................................. C07C 5/00; C07C 5/22
[52] U.S. Cl. ......................... 585/319; 585/481; 585/482; 585/478; 585/477
[58] Field of Search ..................... 585/319, 481, 585/482, 478, 477, 415

[56] References Cited

U.S. PATENT DOCUMENTS

| | | | |
|---|---|---|---|
| 3,553,276 | 1/1971 | Berger et al. | 260/668 |
| 3,998,900 | 12/1976 | Wilhelm | 260/668 D |
| 4,062,903 | 12/1977 | Jacobson | 260/668 A |
| 4,593,138 | 6/1986 | Casci et al. | 585/481 |
| 6,057,486 | 5/2000 | Merlen et al. | 585/481 |

FOREIGN PATENT DOCUMENTS

| | | |
|---|---|---|
| 0 051 318 | 5/1982 | European Pat. Off. . |
| 50-16780 | 6/1975 | Japan . |
| 96/16004 | 5/1996 | WIPO . |

*Primary Examiner*—Marian C. Knode
*Assistant Examiner*—Thuan D. Dang
*Attorney, Agent, or Firm*—Millen, White, Zelano & Branigan, P.C.

[57] ABSTRACT

A $C_8$ aromatic feedstock is isomerized by an isomerization stage conducted at 320–380° C. with a catalyst containing at least one EUO-structure-type zeolite and at least one metal of group VIII, to obtain an effluent containing isomerized alkyl aromatics and about 10–30% by weight of naphthenes. The effluent is then subjected to a dehydrogenation stage so as to convert the naphthenes to additional alkyl aromatics.

20 Claims, 2 Drawing Sheets

ISOMERIZATION WITH AN EUO-TYPE CATALYST OF AROMATIC COMPOUNDS WITH EIGHT CARBON ATOMS FOLLOWED BY A DEHYDROGENATION STAGE

CROSS REFERENCE TO RELATED APPLICATION

This application is related to a co-assigned concurrently filed application entitled "Process For Activating Catalysts For Isomerising Aromatic Compounds Containing Eight Carbon Atoms" the inventors being, Jean-François Joly, Julia Magne-Drisch, Fabio Alario, Elisabeth Merlen, Eric Benazzi and Sylvie Lacombe, based on priority French application 98/04.651 filed Apr. 10, 1998, said application being incorporated by reference herein.

FIELD OF THE INVENTION

This invention relates to the area of the isomerization processes of aromatic compounds with eight carbon atoms.

BACKGROUND OF THE INVENTION

According to the known processes for isomerization of aromatic compounds with eight carbon atoms, a feedstock that is generally low in paraxylene relative to the thermodynamic equilibrium of the mixture (i.e., whose paraxylene content is clearly less than that of the mixture with the thermodynamic equilibrium at the temperature in question, whereby this mixture comprises at least one compound that is selected from the group that is formed by metaxylene, orthoxylene, paraxylene and ethylbenzene) and generally rich in ethylbenzene relative to this same mixture in thermodynamic equilibrium is introduced into a reactor that contains at least one catalyst under suitable temperature and pressure conditions to obtain a composition, at the outlet of said reactor, of aromatic compounds with eight carbon atoms that is as close as possible to the composition of said mixture in thermodynamic equilibrium at the temperature of the reactor.

Paraxylene and optionally orthoxylene, which are the desired isomers because they exhibit an important advantage particularly for the synthetic fiber industry, are then separated from this mixture. Metaxylene and ethylbenzene can then be recycled to the inlet of the isomerization reactor so as to increase the production of paraxylene and orthoxylene. When it is not desired to recover orthoxylene, the latter is recycled with metaxylene and ethylbenzene.

The isomerization reactions of the aromatic compounds with eight carbon atoms per molecule pose, however, several problems that are produced by secondary reactions. Thus, in addition to the main isomerization reaction, hydrogenation reactions are observed, such as, for example, the hydrogenation of the aromatic compounds to naphthenes, reactions of opening naphthene cycles that lead to the formation of paraffins that have at most the same number of carbon atoms per molecule as the naphthenes from which they are obtained. Cracking reactions are also observed, such as, for example, the cracking of paraffins that lead to the formation of light paraffins that typically have from 3 to 5 carbon atoms per molecule, dismutation and transalkylation reactions that lead to the production of benzene, toluene, aromatic compounds with nine carbon atoms per molecule (trimethylbenzenes, for example) and heavier aromatic compounds.

All of these secondary reactions are greatly detrimental to the yields of desired products.

The amount of secondary products that are formed (naphthenes that typically contain from 5 to 8 carbon atoms, paraffins that contain from 3 to 8 carbon atoms, benzene, toluene, aromatic compounds with, for the most part, 9 and 10 carbon atoms per molecule) depends on the nature of the catalyst and the operating conditions of the isomerization reactor (temperature, partial hydrogen and hydrocarbon pressures, feedstock flow rate).

It is well known to one skilled in the art that the secondary reactions increase when the paraxylene content in the reactor is closer to the paraxylene content in thermodynamic equilibrium under given pressure and temperature conditions.

The optimization of the operating conditions as well as the optimization of the formulation of the isomerization catalyst make it possible to improve the paraxylene yield but not to be loss-free. In addition, the search for obtaining new catalysts is a long and costly activity.

We have discovered, in a surprising way, that it is possible to reach paraxylene contents that are close to the paraxylene content in thermodynamic equilibrium while reducing the xylene losses by combining at least two reaction stages.

SUMMARY OF THE INVENTION

Thus, this invention relates to a process for isomerization of a feedstock that contains aromatic compounds with eight carbon atoms and that comprises at least one isomerization stage a) that is carried out in the presence of a catalyst that contains at least one EUO-structure-type zeolite and at least one metal of group VIII of the periodic table (Handbook of Chemistry and Physics, 45th Edition, 1964–1965) and at least one dehydrogenation stage b). This invention also relates to apparatus for conducting this process. According to a particular embodiment of this invention, the feedstock that is treated in the isomerization stage contains at least ethylbenzene and/or at least metaxylene or at least a mixture of ethylbenzene and metaxylene.

The EUO-structure-type zeolite is selected from among the zeolites: EU-1, TPZ-3 and ZSM-50.

The isomerization catalysts that are used in stage a) of the process according to the invention are all catalysts that contain an EUO-structure-type zeolite and a metal from group VIII that, starting from a mixture that contains aromatic compounds with eight carbon atoms including xylenes and/or ethylbenzene, make it possible to obtain a composition of the mixture—xylenes and ethylbenzene—that is close to that of the composition of the mixture in thermodynamic equilibrium under given temperature and pressure conditions.

Any catalyst that makes it possible to dehydrogenate naphthene-type compounds into aromatic compounds can be used in stage b) of the process according to this invention. At the outlet of the dehydrogenation reactor, for a given number of carbon atoms per molecule, the aromatic compounds that are obtained are in proportions of thermodynamic equilibrium under the outlet temperature and pressure conditions of this reactor.

The catalysts that are used in stage a) of the process according to the invention are catalysts that most often have an alumina base as a substrate and that comprise at least one EUO-structure-type zeolite, such as, for example, the EU-1 zeolite and at least one metal or a metal compound of group VIII. The metal of group VIII is usually selected from among the noble metals or the noble metal compounds of this group VIII and in particular platinum or palladium or a compound of at least one of these metals and preferably platinum or a platinum compound will be used. The matrix, or binder, ensures the make-up to 100% by weight in the catalyst.

In a preferred way, a catalyst that comprises at least one EUO-structure-type zeolite that is at least partially in acid form, for example, the EU-1 zeolite, is used. The EUO-structure-type zeolite that is used contains silicon and at least one element T that is selected from the group that is formed by aluminum, iron, gallium and boron, preferably aluminum and boron, and whose overall Si/T atomic ratio is about 5 to 100, preferably about 5 to 80, and still more preferably about 5 to 60. This catalyst also comprises at least one matrix (or binder), at least one metal or a metal compound of group VIII of the periodic table. This catalyst also optionally comprises at least one metal or a metal compound that is selected from the group that is formed by the metals or metal compounds of groups IIIA and IVA of the periodic table, and optionally sulfur or at least one sulfur compound.

The matrix is generally selected from the group that is formed by natural clays (for example, kaolin or bentonite), synthetic clays, magnesia, aluminas, silicas, silica-aluminas, titanium oxide, boron oxide, zirconia, aluminum phosphates, titanium phosphates, zirconium phosphates, preferably from among the elements of the group that is formed by the aluminas and the clays. This matrix can be a single compound or a mixture of at least two of these compounds.

The EUO-structure-type zeolite is at least partially, preferably virtually totally, in acid form, i.e., in hydrogen form ($H^+$).

This catalyst optionally also contains at least one additional element that is selected from the complex that is formed by groups IIIA and IVA of the periodic table, preferably selected from the group that is formed by tin and indium.

In the first stage of the process according to this invention, the operating conditions of the isomerization zone are selected to reduce the production of undesirable compounds that are obtained from reactions that cause acid catalysis mechanisms to take effect (cracking, dealkylation, dismutation). These operating conditions are such that the production of naphthenes with eight carbon atoms per molecule is significantly larger—about 10 to 30% by weight of the effluent output of the isomerization zone—than the production that is obtained by the standard isomerization processes of aromatic compounds that contain eight carbon atoms—which is generally from about 5 to 10% by weight of the effluent output of the isomerization zone.

The effluent that is obtained at the end of the first reaction stage is treated during a second stage in a reaction zone that contains at least one dehydrogenation catalyst. The operating conditions of this second stage can be different or identical to the operating conditions of the first stage, preferably the operating conditions of these two stages are different. The operating conditions of this second stage are determined so as to obtain a composition of the mixture of xylenes and ethylbenzene that is closest to the composition in thermodynamic equilibrium.

The catalysts for dehydrogenation of paraffins and naphthenes are well known to one skilled in the art. The substrates of these catalysts are generally refractory oxides; most often an alumina is selected. These dehydrogenation catalysts comprise at least one noble metal of group VIII of the periodic table and at least one alkaline element or alkaline earth element of groups Ia and IIa of the periodic table. Preferably, the noble metal of group VIII that is selected is platinum, and the element of groups Ia or IIa of the periodic table is selected from the group that comprises magnesium, potassium, calcium and lithium.

These dehydrogenation catalysts can also contain thorium and/or at least one element M of groups IVa or IVb of the periodic table. The elements of groups IVa or IVb are most often selected from the group that is formed by tin, silicon, titanium and zirconium. Some dehydrogenation catalysts also contain sulfur and/or a halogen. More particularly, it is possible to use the dehydrogenation catalysts that are described in Patents U.S. Pat. No. 3,998,900 and U.S. Pat. No. 3,531,543 in the dehydrogenation stage of the process according to this invention.

Without wanting to be tied to any particular theory, it is noted that platinum exhibits a hydrogenolyzing activity that is expressed to the detriment of the activity of the dehydrogenation of naphthenes into aromatic compounds. This hydrogenolyzing activity can be greatly reduced, and the selectivity of the catalyst relative to the dehydrogenation reaction can be increased by the adding additional element M.

The refractory inorganic substrates that are used often have an acidic nature and can generate undesirable secondary reactions, such as cracking or isomerization reactions. This is why the oxide substrate is generally neutralized by the addition of at least one metal or an alkaline or alkaline-earth metal compound.

According to a preferred embodiment of this invention, at least one compound that has a boiling point of about 80 to about 135° C., preferably at least one compound that is selected from the group that is formed by the paraffins with eight carbon atoms per molecule, benzene, toluene, and naphthenes with eight carbon atoms, is added to the feedstock that is introduced in the isomerization zone.

This compound or these compounds are added to the feedstock that is to be treated in the form of recycling and/or in the form of fresh compounds in amounts such that the percentages per unit of weight of added compounds relative to the total feedstock that enters the reactor are usually as follows:

the percentage of paraffins with eight carbon atoms, in the optional case where this compound is added, is from about 0.1 to 10% by weight, preferably about 0.2 to 2% by weight, the percentage of naphthenes with eight carbon atoms, in the optional case where this compound is added, is from about 0.5 to 15% by weight, and preferably about 2 to 8% by weight, the percentage of toluene, in the optional case where this compound is added, is from about 0.1 to 10% by weight, preferably about 0.2 to 5% by weight, the percentage of benzene, in the optional case where this compound is added, is from about 0.1 to 10% by weight, preferably about 0.2 to 2% by weight.

The percentage of total compounds that are added when several compounds are added represents about 0.1 to 20% by weight and often about 2 to 15% by weight relative to the total feedstock that enters the isomerization zone.

According to a preferred embodiment of the invention, at least two different compounds that each have a boiling point of about 80° C. to 135° C. are introduced into the reaction zone. More particularly, at least one naphthene with eight carbon atoms and at least one paraffin with eight carbon atoms are introduced. In another variant, when these compounds are obtained from recycling of a liquid fraction that leaves the dehydrogenation reactor, all of the compounds that are contained in this liquid fraction that have boiling points of about 80° C. to 135° C. are introduced without being separated.

In the process according to this invention, the isomerization stage is used in the presence of hydrogen that can be introduced in the form of fresh hydrogen, in the form of recycled hydrogen that is obtained from the outlet of the isomerization zone or in the form of recycled hydrogen that is obtained from the outlet of the dehydrogenation zone. The operating conditions of the isomerization stage are as follows: a reaction temperature of about 300 to 500° C., preferably of about 320 to 380° C., a partial hydrogen pressure of about 0.3 to 1.5 MPa, preferably of about 0.4 to 1.2 MPa, a total pressure of about 0.4 to 2 MPa, preferably of about 0.6 to 1.5 MPa and a PPH (feedstock weight/catalyst weight/hour) of about 0.2 to 10 $h^{-1}$, preferably of about 3 to 6 $h^{-1}$.

In the process according to this invention, the dehydrogenation stage is used in the presence of hydrogen that can be introduced in the form of fresh hydrogen, in the form of recycled hydrogen that is obtained from the outlet of the isomerization zone or in the form of recycled hydrogen that is obtained from the outlet of the dehydrogenation zone.

The operating conditions for the dehydrogenation stage are a temperature of about 300 to 500° C., preferably of about 400 to 420° C., a partial absolute hydrogen pressure of about 0.1 to 1.5 MPa, preferably of about 0.4 to 1 MPa, a total absolute pressure of about 0.2 to 2 MPa, preferably of about 0.5 to 1.5 MPa and a PPH (feedstock weight/catalyst weight/hour) of about 0.2 to 10 $h^{-1}$, preferably of about 3 to 6 $h^{-1}$.

This invention also relates to apparatus for conducting the process according to the invention that comprises at least one pipe for bringing the feedstock into an isomerization zone, at least one pipe for bringing hydrogen into the isomerization zone, at least one isomerization zone that comprises a catalyst that contains an EUO-structural-type zeolite and at least one noble metal from group VIII, at least one pipe through which the effluent of said isomerization zone is introduced into a hydrogen separation zone, at least one hydrogen separation zone, at least one pipe through which hydrogen is evacuated, at least one pipe through which the effluent of said hydrogen separation zone that does not contain hydrogen is introduced into a furnace, at least one furnace, at least one pipe through which the effluent of said furnace is sent into a dehydrogenation zone, at least one pipe for bringing hydrogen into the dehydrogenation zone, at least one dehydrogenation zone, at least one pipe through which the effluent of said dehydrogenation zone is sent into a second hydrogen separation zone, at least a second hydrogen separation zone, at least one pipe through which the hydrogen is evacuated and at least one pipe for evacuation of the effluent that does not contain hydrogen.

In addition, it is also possible to carry out a recycling of aromatic compounds with eight carbon atoms that are contained in the effluent of the dehydrogenation zone after the desired compounds, i.e., paraxylene and optionally orthoxylene, have been extracted.

According to this variant, the device according to this invention also comprises at least one zone for separating aromatic compounds that contain eight carbon atoms, at least one pipe for evacuating aromatic compounds that contain eight carbon atoms, at least one pipe for evacuating compounds other than the aromatic compounds that contain eight carbon atoms, at least one zone for separating compounds with a boiling point of about 80 to 135° C., at least one pipe for recycling these compounds to the isomerization zone and at least one pipe for evacuating the remainder of the effluent.

DETAILED DESCRIPTION OF THE DRAWINGS

Figure 1:
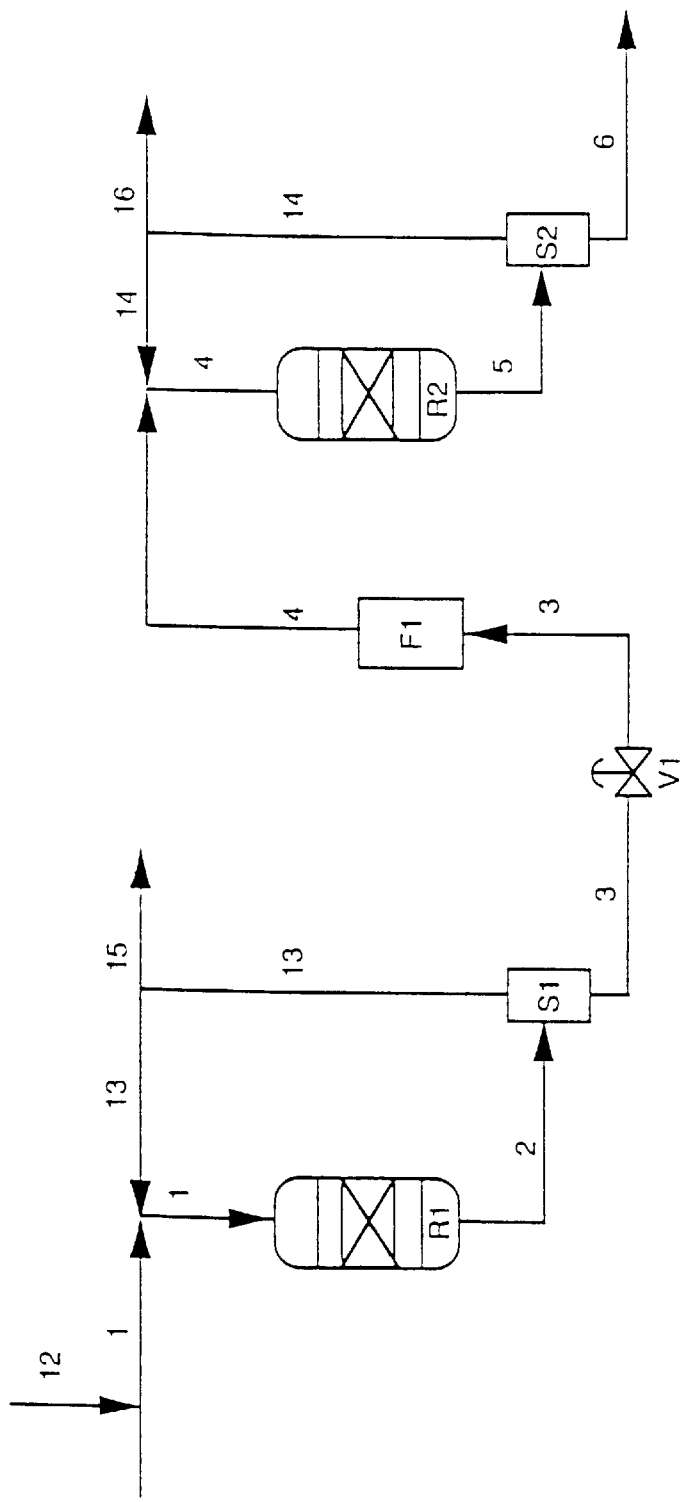
FIG. 1 is a flowsheet depicting a simple embodiment of the process according to the invention.

According to FIG. 1, the feedstock that is to be treated is introduced into isomerization zone R1 that comprises a catalyst that contains an EUO-structural-type zeolite and at least one noble metal of group VIII via line 1. Essentially pure hydrogen is introduced into line 1 via line 12 and the recycled hydrogen is introduced into line 1 via line 13. A purging of the hydrogen that circulates in line 13 is carried out via line 15. The effluent of isomerization zone R1 is sent into a separation zone S1 via line 2. In S1, the hydrogen that is contained in the effluent is isolated and recycled to the inlet of isomerization zone R1 via line 13, and the remainder of the effluent is evacuated from this separation zone S1 via line 3. This line 3 is equipped with a pressure regulating valve V1. The fluid that is contained in line 3 is heated in a furnace F1 and then is evacuated from this furnace via line 4. The effluent that leaves from the furnace via line 4 is enriched with hydrogen that is recycled via line 14, and then this mixture is introduced into dehydrogenation zone R2. The effluent of zone R2 is sent via line 5 into separation zone S2. In S2, the hydrogen that is contained in the effluent is isolated and recycled to the inlet of dehydrogenation zone R2 via line 14, and the remainder of the effluent is evacuated from separation zone S2 via a line 6. A purging of the hydrogen that circulates in line 14 is carried out via line 16.

Figure 2:
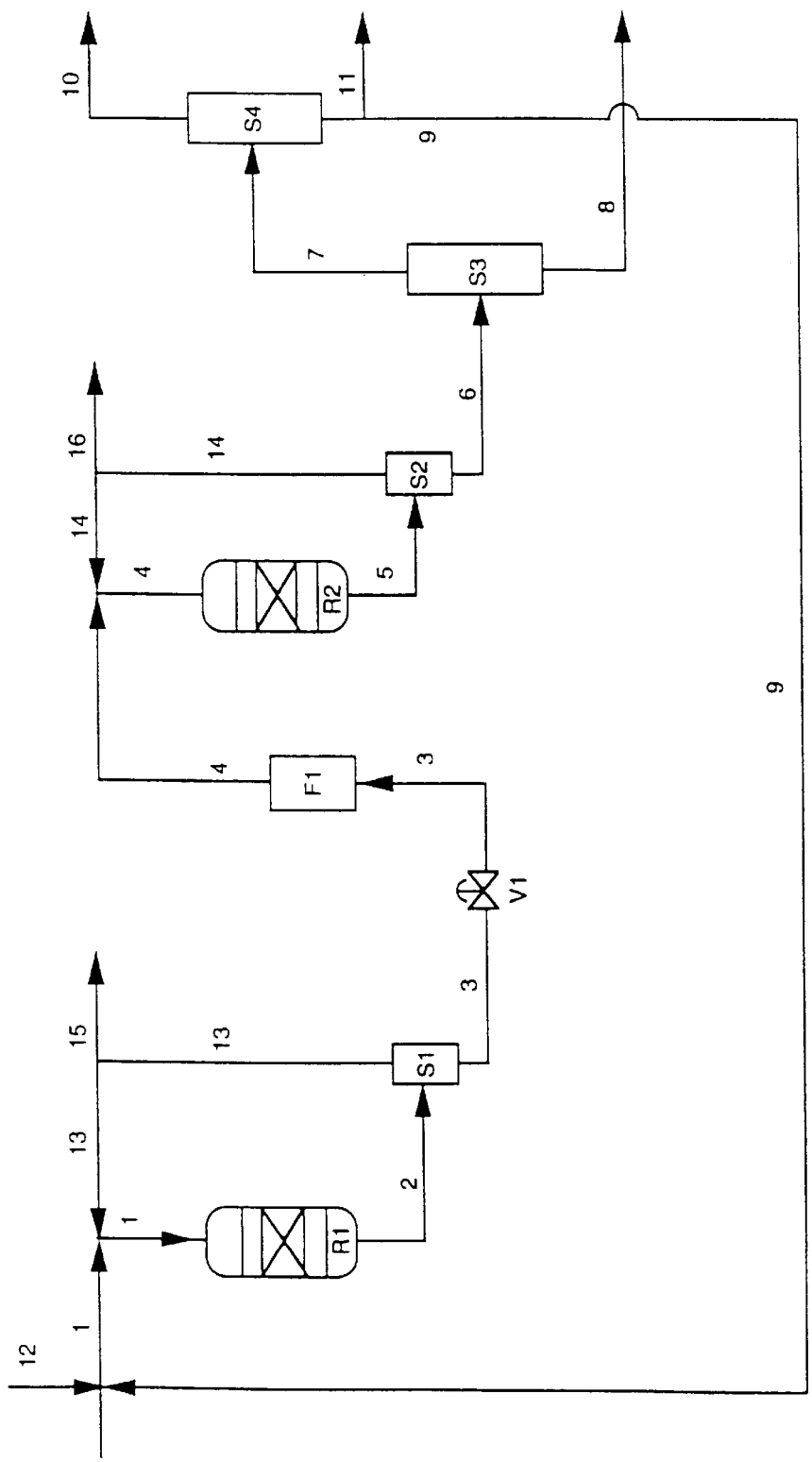
FIG. 2 is a flowsheet depicting a preferred embodiment of the process according to the invention.

According to FIG. 2, the feedstock that is to be treated is introduced into isomerization zone R1 via line 1. Before being injected into isomerization zone R1, this fresh feedstock is enriched via line 9 with a recycling mixture that contains at least one compound that is selected from the group that is formed by paraffins with eight atoms of carbon, benzene, toluene and naphthenes with eight carbon atoms. Essentially pure hydrogen is introduced into line 1 via line 12, and recycled hydrogen is introduced into line 1 via line 13. A purging of the hydrogen that circulates in line 13 is carried out via line 15.

The effluent of isomerization zone R1 is sent into a separation zone S1 via line 2. In S1, the hydrogen that is contained in the effluent is isolated and recycled to the inlet of isomerization zone R1 via line 13, and the remainder of the effluent is evacuated from this separation zone S1 via line 3. This line 3 is equipped with a pressure regulating valve V1. The fluid that is contained in line 3 is heated in a furnace F1 and then is evacuated from this furnace via line 4. The effluent that leaves the furnace via line 4 is enriched with hydrogen that is recycled via line 14, and then this mixture is introduced into dehydrogenation zone R2. The effluent of zone R2 is sent via line 5 into separation zone S2. In S2, the hydrogen that is contained in the effluent is isolated and recycled to the inlet of dehydrogenation zone R2 via line 14, and the remainder of the effluent is evacuated from separation zone S2 and is introduced into separation zone S3 via a line 6. A purging of the hydrogen that circulates in line 14 is carried out via line 16. In this separation zone S3, the products of the reaction are separated into two fractions: a light fraction that contains paraffins, naphthenes as well as the lightest aromatic compounds—benzene and toluene—is sent via line 7 into a separation zone S4: the other fraction comprises the aromatic compounds that contain at least eight carbon atoms, and this fraction is evacuated from the device via line 8.

In separation zone S4, the compounds with a boiling point of about 80 to 135° C. are separated from the other hydrocarbons. The compounds with boiling points of about 80 to 135° C. are evacuated from S4 via line 9, a purging of a portion of these compounds is carried out via line 11, and the other portion of these compounds with a boiling point of about 80 to 135° C. that circulate in line 9 feeds the flow of line 1. The lighter hydrocarbons (i.e., with a boiling point that is less than 80° C.) are evacuated from the device via line 10.

The following examples illustrate the invention without limiting its scope.

The catalyst that is used in stage a) is obtained via the procedure that is described below.

The base material that is used is an EUO-structural-type zeolite, the EU-1 zeolite, raw straight from synthesis, that comprises the organic structure, silicon and aluminum, and that has an overall Si/Al atomic ratio that is equal to 13.6, a content by weight of sodium relative to the dry EU-1 zeolite weight of 1.5%, corresponding to an Na/Al atomic ratio of 0.6.

This EU-1 zeolite first undergoes a so-called dry calcination at 550° C. under a stream of air for 6 hours. Then, the solid that is obtained is subjected to three ionic exchanges in a 10N solution of $NH_4NO_3$ at about 100° C. for 4 hours for each exchange.

At the end of these treatments, the EU-1 zeolite in $NH_4$ form has an overall Si/Al atomic ratio that is equal to 18.3, a content by weight of sodium relative to the dry EU-1 zeolite weight of 50 ppm, corresponding to an Na/Al atomic ratio of 0.003, a specific surface area that is measured by the BET method of 407 $m^2/g$ and a pore volume, with nitrogen, that is measured at −196° C. and at $P/P_o$=0.15, with 0.16 $cm^3$ of liquid nitrogen per gram. In the EU-1 zeolite, 100% of the aluminum atoms are in a tetrahedral coordination number according to NMR analysis of aluminum 27.

The EU-1 zeolite is then shaped by extrusion with an alumina gel to obtain, after drying and calcination in dry air, substrate S1 that consists of extrudates that are 1.4 mm in diameter and that contains 10% by weight of EU-1 zeolite in H form and 90% of alumina.

Substrate S1 that is thus obtained is subjected to an anionic exchange with hexachloroplatinic acid in the presence of a competing agent (hydrochloric acid) so as to introduce 0.3% by weight of platinum relative to the catalyst. The moist solid is then dried at 120° C. for 12 hours and calcined under a flow of dry air at the temperature of 500° C. for one hour.

Catalyst C1 that is thus obtained contains 10.0% by weight of EU-1 zeolite in H form, 89.7% of alumina and 0.29% of platinum.

The dehydrogenation catalyst that is used in stage b) is a catalyst with an alumina base that contains 0.6% by weight of platinum, 0.9% by weight of tin, 0.9% by weight of potassium and 0.6% by weight of chlorine.

EXAMPLE 1

According to the Invention

A pilot unit according to FIG. 1 that is attached to this text and that comprises two reactors in series, whereby each is equipped with a hydrogen recycling and a pressure regulating valve is placed between the two reactors, is used. Each of the reactors is heated electrically and operates according to an isothermal mode.

Each reactor contains 60 g of catalyst that is specific to each stage and that is described above.

The feedstock that is to be converted is a mixture of aromatic compounds with eight carbon atoms, and its composition is given in Table 1 below.

The feedstock flow rate is equal to 180 g/h.

The operating conditions are as follows.

In isomerization reactor (R1), the temperature is 375° C., the partial pressure of hydrogen is 1.04 MPa and the total pressure is 1.3 MPa.

In dehydrogenation reactor (R2), the temperature is 400° C., the partial hydrogen pressure is 6 bar absolute and the total pressure is 9 bar absolute.

The compositions per unit of weight of the feedstock and effluent output of each of the reactors are indicated in Table 1 below.

In the tables below, the following abbreviations are used: "C1–C6 paraffins" for paraffins that contain from 1 to 6 carbon atoms, "C5 to C9 naphthenes" for naphthenes that contain 5 to 9 carbon atoms, and "C9+ aromatic compounds" for aromatic compounds that contain nine or more carbon atoms.

TABLE 1

| Compounds | Input | Outlet R1 | Outlet R2 |
|---|---|---|---|
| C1–C6 paraffins | 0 | 0.77 | 0.91 |
| C5 to C9 naphthenes | 0 | 20.59 | 2.20 |
| benzene | 0 | 0.04 | 0.07 |
| toluene | 0 | 0.26 | 0.32 |
| ethylbenzene | 14.01 | 7.20 | 8.58 |
| paraxylene | 1.52 | 15.99 | 20.36 |
| metaxylene | 56.52 | 37.23 | 46.69 |
| orthoxylene | 27.95 | 17.28 | 20.05 |
| C9 + aromatic compounds | 0 | 0.64 | 0.82 |

EXAMPLE 2

Comparative

For Example 2, a single reactor (R) is used with the same isomerization catalyst as the one that is used in Example 1. The feedstock that is to be treated is identical to that of Example 1. The feedstock flow rate is identical to that of Example 1. The operating conditions are those of the dehydrogenation reaction of Example 1: the temperature is 400° C., the partial hydrogen pressure is 0.6 MPa and the total pressure is 0.9 MPa. By setting these operating conditions, a content of naphthenes that contain 5 to 9 carbon atoms at the outlet of the reactor is dictated close to that obtained at the outlet of dehydrogenation reactor (R2) of Example 1.

The compositions per unit of weight of the feedstock and the effluent that leaves the reactor are indicated in Table 2 below:

TABLE 2

| Compounds | Inlet | Outlet R |
|---|---|---|
| C1–C6 paraffins | 0 | 1.32 |
| C5 to C9 naphthenes | 0 | 2.46 |
| benzene | 0 | 0.31 |
| toluene | 0 | 2.00 |
| ethylbenzene | 14.01 | 10.91 |
| paraxylene | 1.52 | 19.09 |
| metaxylene | 56.52 | 42.65 |
| orthoxylene | 27.95 | 18.26 |
| C9 + aromatic compounds | 0 | 3.00 |

The composition per unit of weight of the effluent that leaves the second reactor of Example 1 and the composition per unit of weight of the effluent that leaves the reactor of Example 2 are recorded in Table 3.

TABLE 3

| Compounds | Outlet R | Outlet R2 |
| --- | --- | --- |
| C1–C6 paraffins | 1.32 | 0.91 |
| C5 to C9 naphthenes | 2.46 | 2.20 |
| benzene | 0.31 | 0.07 |
| toluene | 2.00 | 0.32 |
| ethylbenzene | 10.91 | 8.58 |
| paraxylene | 19.09 | 20.36 |
| metaxylene | 42.65 | 46.69 |
| orthoxylene | 18.26 | 20.05 |
| C9 + aromatic compounds | 3.00 | 0.82 |

Table 3 clearly demonstrates the advantage that there is in using the process according to this invention with two reactors in series that contain two different catalysts. To compare the effectiveness of the two processes (process according to this invention and standard process according to the prior art), we have chosen to apply in Example 2 the operating conditions of dehydrogenation of Example 1; we thus obtain comparable amounts of naphthenes that contain 5 to 9 carbon atoms (C5 to C9 naphthenes) at outlet R and at outlet R2.

Under these conditions, when the process according to the invention is used (Example 1), the amount of paraxylene that is produced is 20.36% by weight as opposed to 19.09% by weight when the standard isomerization process is used (Example 2); the output of aromatic compounds with eight carbon atoms is also larger than 95.68% by weight when the process according to the invention is used as opposed to 90.91% by weight when the standard isomerization process is used.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above, and of corresponding French application 98/04650, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for isomerization of a feedstock that contains aromatic compounds with eight carbon atoms comprising subjecting the feedstock in the vapor phase to at least one isomerization stage a) conducted at 320–380° C. in the presence of a catalyst containing at least one zeolite having and EUO structure at least partially in acid form and at least one metal of group VIII, to obtain an effluent containing isomerized alkyl aromatic compounds and 10–30% by weight of naphthenes based on the total weight of the effluent, and subjecting said effluent to at least one catalytic dehydrogenation stage b), to convert said naphthenes substantially to aromatic compounds.

2. A process for isomerization according to claim 1, wherein the feedstock treated in the isomerization stage contains at least ethylbenzene or at least metaxylene or at least a mixture of ethylbenzene and metaxylene.

3. A process for isomerization according to claim 1, wherein the zeolite is EU-1, ZSM-50, or TPZ-3.

4. A process of isomerization according to claim 1, wherein the catalyst comprises at least one matrix, at least one element of group VIII and at least one zeolite having an EUO structure, said zeolite containing silicon and at least one element T selected from the group consisting of aluminum, iron, gallium and boron, such that the overall Si/T atomic ratio is about 5 to 100.

5. A process for isomerization according to claim 1, wherein the isomerization reaction of stage a) is carried out at a partial absolute hydrogen pressure of about 0.3 to 1.5 MPa, at a total absolute pressure of about 0.4 to 2 MPa and at a PPH (feedstock weight/catalyst weight/hour) of about $0.2\ h^{-1}$ to $10\ h^{-1}$.

6. A process for isomerization according to claim 1, wherein the catalyst used for carrying out the dehydrogenation reaction of stage b) comprises a substrate that contains at least one refractory oxide, at least one noble metal of group VIII and at least one element of groups Ia or IIa.

7. A process for isomerization according to claim 6, wherein the catalyst used for carrying out the dehydrogenation reaction of stage b) further comprises at least one element that is selected from the group consisting of thorium and elements of groups IVa and IVb.

8. A process for isomerization according to claim 1, wherein the dehydrogenation reaction of stage b) is carried out at a temperature of about 400° C. to 420° C., at a partial absolute hydrogen pressure of about 0.1 to 1.5 MPa, at a total absolute partial pressure of about 0.2 to 2 MPa and at a PPH (feedstock weight/catalyst weight/hour) of about $0.20\ h^{-1}$ to $10\ h^{-1}$.

9. A process for isomerization according to claim 1, wherein at least one compound that has a boiling point of about 80 to about 135° C. is added to the feedstock in the form of recycling or in the form of fresh compounds or in the form of recycling and fresh compounds.

10. A process for isomerization according to claim 9, wherein the added compound represents about 0.1 to 20% by weight of the total feedstock that enters the isomerization zone.

11. A process of isomerization according to claim 3, wherein the catalyst comprises at least one matrix, at least one element of group VIII and at least one zeolite having an EUO structure, said zeolite containing silicon and at least one element T selected from the group consisting of aluminum, iron, gallium and boron, such that the overall Si/T atomic ratio is about 5 to 100.

12. A process for isomerization according to claim 11, wherein the catalyst used for carrying out the dehydrogenation reaction of stage b) comprises a substrate that contains at least one refractory oxide, at least one noble metal of group VIII and at least one element of groups Ia or IIa.

13. A process for isomerization according to claim 12, wherein the catalyst used for carrying out the dehydrogenation reaction of stage b) further comprises at least one element that is selected from the group consisting of thorium and elements of groups IVa and IVb.

14. A process for isomerization according to claim 13, wherein the dehydrogenation reaction of stage b) is carried out at a temperature of about 400° C. to 420° C., at a partial absolute hydrogen pressure of about 0.1 to 1.5 MPa, at a total absolute partial pressure of about 0.2 to 2 MPa and at a PPH (feedstock weight/catalyst weight/hour) of about $0.20\ h^{-1}$ to $10\ h^{-1}$.

15. A process according to claim 1, wherein the content of naphthenes in said effluent is higher than the content of paraxylene.

16. A process according to claim 1, wherein the at least one zeolite is EU-1 and the at least one group VIII metal is platinum.

17. A process according to claim 14, wherein the at least one zeolite is EU-1 and the at least one group VIII metal is platinum.

18. A process according to claim 6, wherein the substrate of the catalyst for the dehydrogenation reaction is alumina.

19. A process according to claim 17, wherein the substrate of the catalyst for the dehydrogenation reaction is alumina.

20. A process according to claim 19, wherein said catalyst for the dehydrogenation reaction comprises platinum, tin, potassium and chlorine.

* * * * *